US012226553B2

(12) United States Patent
Inoue et al.

(10) Patent No.: US 12,226,553 B2
(45) Date of Patent: Feb. 18, 2025

(54) AROMA PROVIDING DEVICE

(71) Applicant: SONY GROUP CORPORATION, Tokyo (JP)

(72) Inventors: Yukito Inoue, Tokyo (JP); Shuji Fujita, Tokyo (JP); Cedric Duvert, Tokyo (JP); Akihiko Yoshida, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 692 days.

(21) Appl. No.: 17/433,513

(22) PCT Filed: Jan. 22, 2020

(86) PCT No.: PCT/JP2020/002046
§ 371 (c)(1),
(2) Date: Aug. 24, 2021

(87) PCT Pub. No.: WO2020/179256
PCT Pub. Date: Sep. 10, 2020

(65) Prior Publication Data
US 2022/0143254 A1 May 12, 2022

(30) Foreign Application Priority Data

Mar. 6, 2019 (JP) .................. 2019-040802

(51) Int. Cl.
*A61L 9/12* (2006.01)
*A45D 34/02* (2006.01)
*A45D 34/00* (2006.01)

(52) U.S. Cl.
CPC .............. *A61L 9/122* (2013.01); *A45D 34/02* (2013.01); *A45D 2034/005* (2013.01);
(Continued)

(58) Field of Classification Search
None
See application file for complete search history.

(56) References Cited

U.S. PATENT DOCUMENTS

2002/0018181 A1  2/2002  Manne
2018/0025864 A1  1/2018  Katsuraku et al.

FOREIGN PATENT DOCUMENTS

CN  108352141 A  7/2018
DE  69835086 T2  5/2007
(Continued)

OTHER PUBLICATIONS

Nakayama, K. JP2010167168A—translated document (Year: 2010).*
(Continued)

*Primary Examiner* — Jelitza M Perez
(74) *Attorney, Agent, or Firm* — CHIP LAW GROUP

(57) ABSTRACT

There is provided an aroma providing device which includes an aromatic holding structure that is detachable and has a plurality of holding spaces in which aromatics are respectively held. The aroma providing device further includes a blower device that supplies air to pass through the holding spaces, a plurality of air supply paths through which the air is introduced into the respective holding spaces, an opening/closing mechanism that includes a member that is deformed by a physical stimulus or a chemical stimulus and switches whether to allow the air to pass through or not for each of the holding spaces and a control unit that controls the opening/closing mechanism.

10 Claims, 12 Drawing Sheets

(52) U.S. Cl.
CPC ...... *A61L 2209/11* (2013.01); *A61L 2209/133* (2013.01); *A61L 2209/134* (2013.01); *A61L 2209/15* (2013.01)

(56) References Cited

FOREIGN PATENT DOCUMENTS

| | | | |
|---|---|---|---|
| EP | 0993625 | A1 | 4/2000 |
| EP | 3232427 | A1 | 10/2017 |
| JP | 2001508888 | A | 7/2001 |
| JP | 2003-310740 | A | 11/2003 |
| JP | 3613615 | B2 | 1/2005 |
| JP | 2009106402 | A * | 5/2009 |
| JP | 2009189410 | A | 8/2009 |
| JP | 2010167168 | A * | 8/2010 |
| JP | 2011-083453 | A | 4/2011 |
| JP | 2013-074476 | A | 4/2013 |
| JP | 2015-205046 | A | 11/2015 |
| JP | 2016522701 | A | 8/2016 |
| JP | 2019-028471 | A | 2/2019 |
| WO | 99/001793 | A1 | 1/1999 |
| WO | 2013/005615 | A1 | 1/2013 |
| WO | 2017/086023 | A1 | 5/2017 |
| WO | 2018/070457 | A1 | 4/2018 |

OTHER PUBLICATIONS

Nishimura et al. JP2009106402A—translated document (Year: 2009).*
Nakayama et al. JP2010167168A—translated document (Year: 2010).*
Extended European Search Report of EP Application No. 20766580.3, issued on Mar. 22, 2022, 07 pages.
International Search Report and Written Opinion of PCT Application No. PCT/JP2020/002046, issued on Mar. 17, 2020, 09 pages of ISRWO.

* cited by examiner

AROMA PROVIDING DEVICE

CROSS REFERENCE TO RELATED APPLICATIONS

This application is a U.S. National Phase of International Patent Application No. PCT/JP2020/002046 filed on Jan. 22, 2020, which claims priority benefit of Japanese Patent Application No. JP 2019-040802 filed in the Japan Patent Office on Mar. 6, 2019. Each of the above-referenced applications is hereby incorporated herein by reference in its entirety.

TECHNICAL FIELD

The present disclosure relates to an aroma providing device.

BACKGROUND ART

Conventionally, a technology related to an aroma providing device for providing an aroma has been proposed. For example, Patent Document 1 discloses an aroma generating device including: an aroma source tank that has a plurality of independent spaces, contains different aroma sources in the respective spaces, and has an inflow hole for allowing blast air from a blower pump to flow into each space and an outflow hole for allowing blast air containing an aroma material from each aroma source to flow out of the space provided at each space; a control valve that performs control to open and close a flow path of blast air from the blower pump for each space; and a drive circuit that drives the blower pump to blow air to each space of the aroma source tank and drives the control valve to open and close a flow path of the blast air for each space.

CITATION LIST

Patent Document

Patent Document 1: Japanese Patent Application Laid-Open No. 2003-310740

SUMMARY OF THE INVENTION

Problems to be Solved by the Invention

Here, the aroma generating device disclosed in Patent Document 1 is configured by integrating an aroma source tank having spaces in which aroma sources are respectively arranged, an active valve array, and a check valve array with screws. Consequently, in a case where the function of an aroma source (aroma component) disappears, it becomes necessary to replace the entire aroma providing device. If the aroma source can be easily replaced or replenished, the aroma providing device can be used for a long period of time.

Then, the present disclosure provides a new and improved aroma providing device that enables a plurality of aromas to be emitted and an aromatic to be replaced or replenished easily.

Solutions to Problems

The present disclosure provides an aroma providing device including: an aromatic holding structure that is detachable and has a plurality of holding spaces in which aromatics are respectively held; a blower device that supplies air to pass through the holding spaces; a plurality of air supply paths through which the air is introduced into the respective holding spaces; an opening/closing mechanism that includes a member that is deformed by a physical stimulus or a chemical stimulus and switches whether to allow the air to pass through or not for each of the holding spaces; and a control unit that controls the opening/closing mechanism.

Effects of the Invention

As described above, it is possible with the present disclosure to emit a plurality of aromas, and replace or replenish an aromatic easily.

Note that the effects described above are not necessarily restrictive, and any of the effects described in this specification, or any other effect that can be grasped from this specification may be produced together with or instead of the effects described above.

MODE FOR CARRYING OUT THE INVENTION

Figure 1:
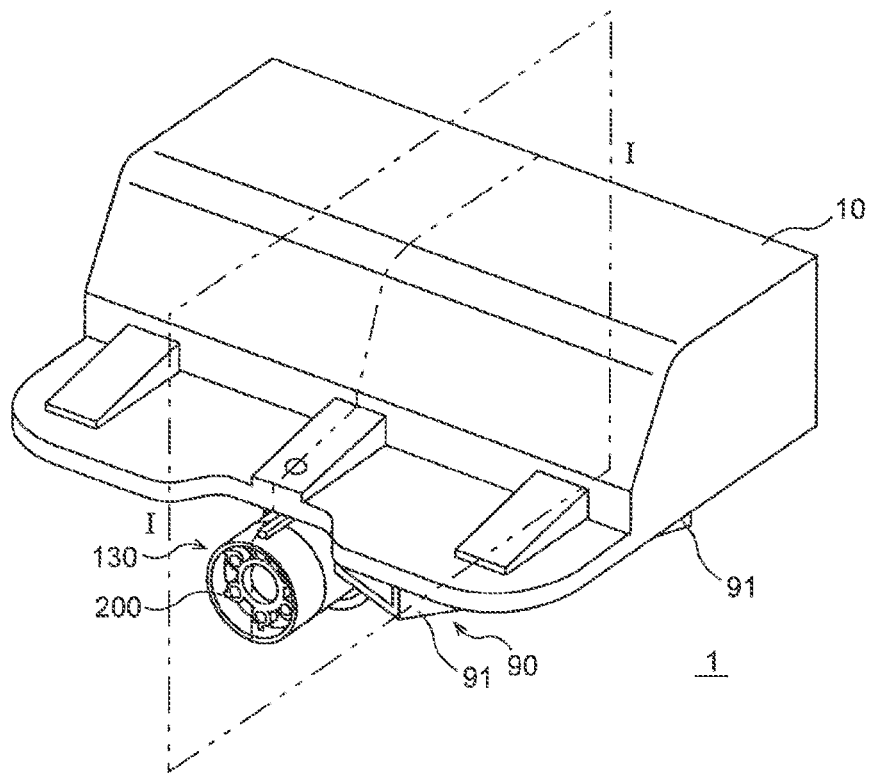
FIG. 1 is a perspective view showing the appearance of an aroma providing device according to an embodiment of the present disclosure.

The following description will explain a preferred embodiment of the present disclosure in detail with reference to the accompanying drawings. In this specification and the drawings, note that components having substantially the same functional configurations are designated by the same reference numerals to omit duplicate description.

Note that the explanations will be given in the following order.

1. Outline of aroma providing device
2. Configuration example of aroma emitting device
3. Configuration example of air emitting device
4. Circuit configuration example
5. Action example
6. Variation In the following description, the emission direction of an aroma is referred to as a front side or a tip side, and the opposite direction is also referred to as a rear side or a rear end side.

<1. Outline of Aroma Providing Device>

Figure 2:
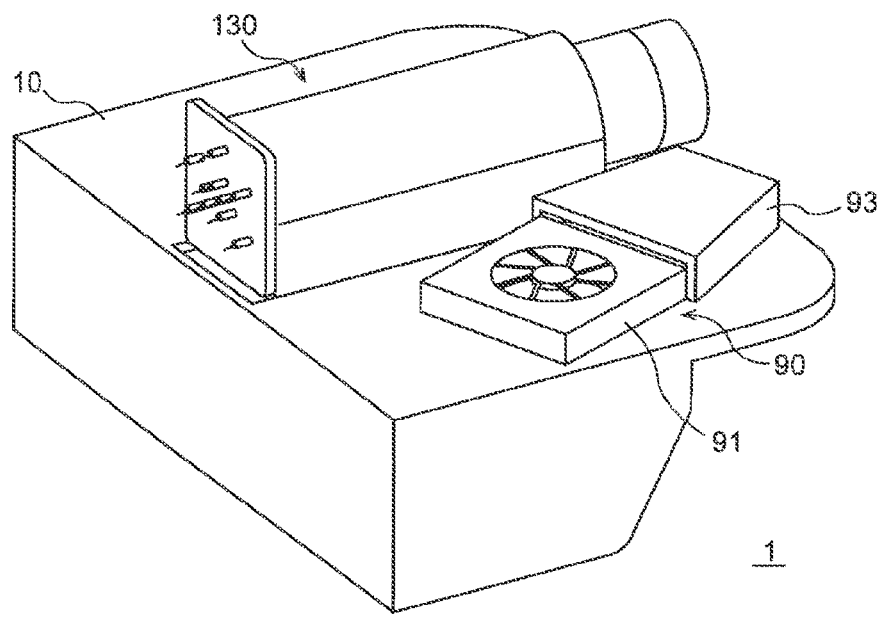
FIG. 2 is a perspective view of an aroma providing device according to the same embodiment as viewed from below.
Figure 3:
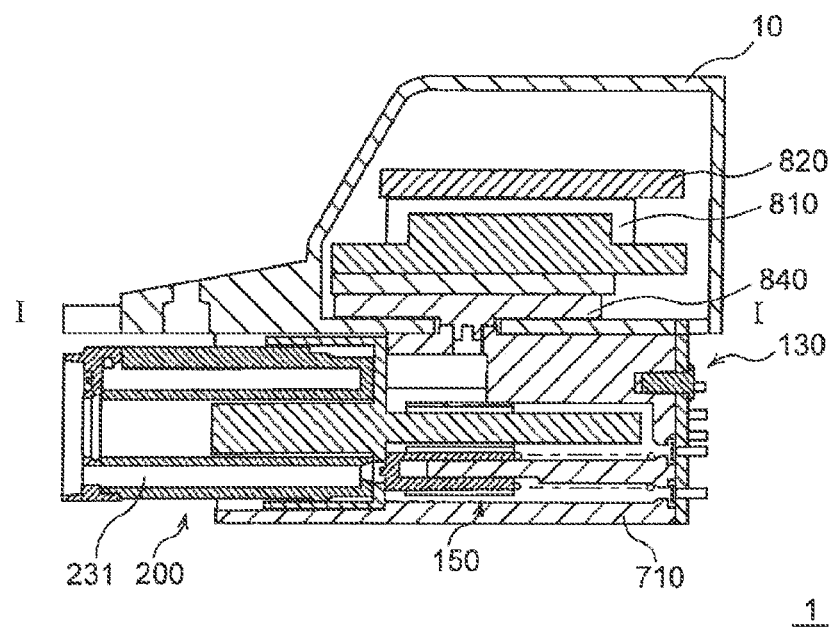
FIG. 3 is a cross-sectional view of an aroma providing device according to the same embodiment.

First, with reference to FIGS. 1 to 3, the outline of an aroma providing device according to an embodiment of the present disclosure will be briefly described. FIG. 1 is a perspective view showing the appearance of an aroma providing device 1 according to the present embodiment, and FIG. 2 is a perspective view of the aroma providing device 1 shown in FIG. 1 as viewed from below. FIG. 3 is a cross-sectional view of the I-I cross section of FIG. 1.

The aroma providing device 1 according to the present embodiment includes a case 10, an aroma emitting device (aroma emitting unit) 130, and an air emitting device (air emitting unit) 90. The aroma emitting device 130 can selectively emit an aroma selected from a plurality of aromas.

The aroma emitting device 130 includes a housing 710, an aromatic cartridge 200, an opening/closing mechanism 150, and a first blower device 840. In the present embodiment, the aromatic cartridge 200 corresponds to an aromatic holding structure. The aromatic cartridge 200 is detachable on the front side of the housing 710.

The aroma emitting device 130 supplies air from the first blower device 840 to each of a plurality of holding spaces 231 (only one is shown in FIG. 3) provided in the aromatic cartridge 200, and vaporizes and emits liquid aromatics held in aromatic holders 251 arranged in the respective holding spaces 231. For example, the aroma emitting device 130 allows the air supplied from the first blower device 840 to pass through a holding space 231 of the aromatic cartridge 200 so as to vaporize a liquid aromatic or an aromatic in a wet state (collectively referred to as "liquid aromatic" hereinafter.) and emit the aromatic from the holding space 231 together with air. The opening/closing mechanism 150 is provided in the housing 710, and opens and closes the flow path of air supplied to each holding space 231.

The first blower device 840 is provided in the case 10. In addition to the first blower device 840, a battery 810 and a circuit board 820 are provided in the case 10. The battery 810 is connected with the first blower device 840 and the opening/closing mechanism 150. The circuit board 820 includes a drive circuit that controls the drive of the first blower device 840, and a drive circuit that controls the drive of the opening/closing mechanism 150. The circuit board 820 controls the drive of the first blower device 840 by controlling power supply from the battery 810 to the first blower device 840, and controls the emission of an aroma by the aroma emitting device 130. Furthermore, the circuit board 820 opens and closes the flow path of air supplied to each holding space 231 by controlling power supply to the opening/closing mechanism 150.

The air emitting device 90 includes a second blower device 91 and a blower duct 93. The second blower device 91 is connected with the battery 810. Furthermore, the circuit board 820 includes a drive circuit that controls the drive of the second blower device 840. The circuit board 820 controls the drive of the second blower device 91 by controlling power supply from the battery 810 to the second blower device 91, and controls the emission of air from the air emitting device 90. The second blower device 91 includes a blower outlet (not shown) on the blower duct 93 side, and a blast generated by the second blower device 91 is introduced into the blower duct 93. The blower duct 93 emits the blast generated by the second blower device 91 in a predetermined direction.

The aroma providing device 1 according to the present embodiment has relatively high straightness and is used as a device that emits an aroma to a limited space. For example, the aroma providing device 1 is attached to a display device for experiencing virtual reality (VR) or augmented reality (AR), and provides an aroma associated with a displayed image. Therefore, the user can experience actual feeling more.

Figure 4:
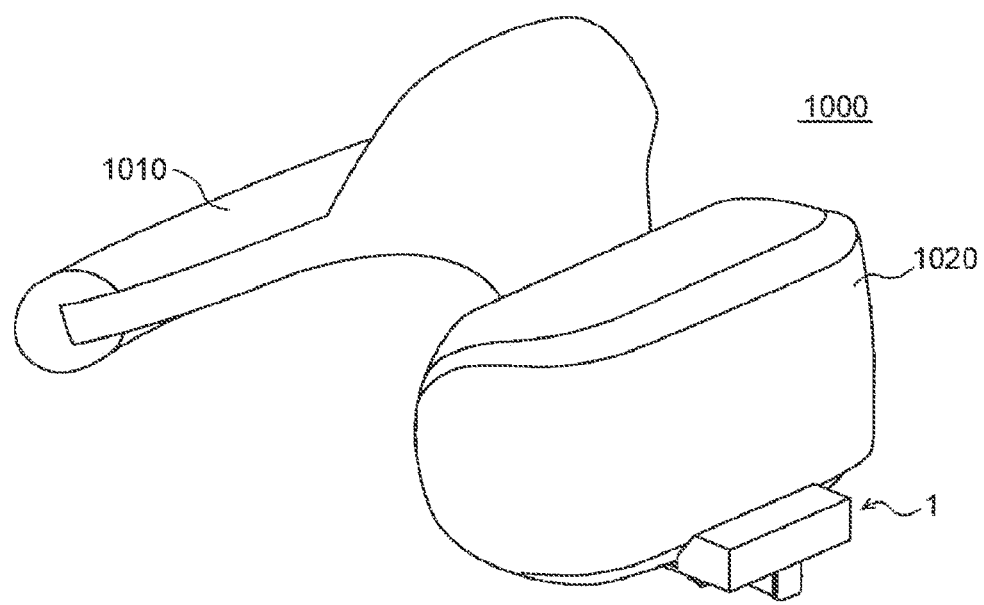
FIG. 4 is a perspective view showing a head-mounted display device including an aroma providing device according to the same embodiment.
Figure 5:
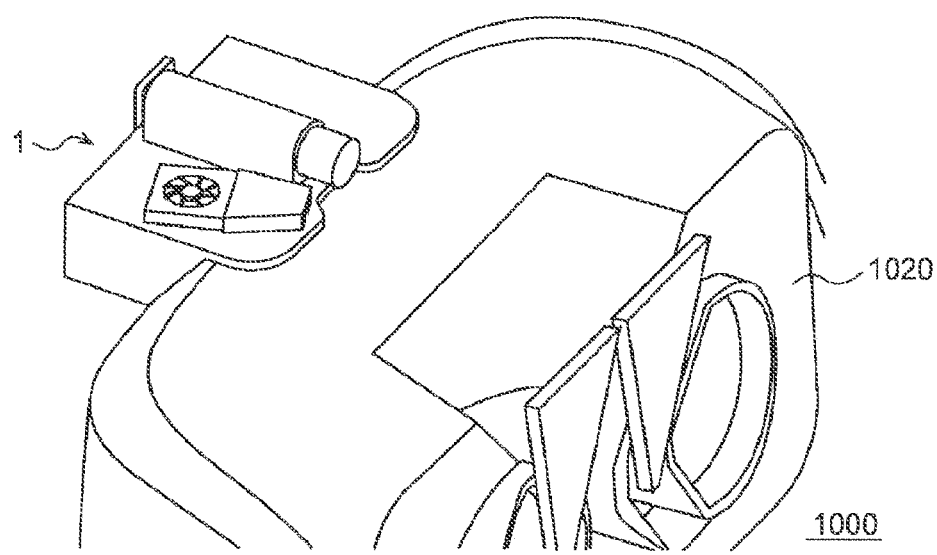
FIG. 5 is a perspective view of a head-mounted display device including an aroma providing device according to the same embodiment as viewed from below.

FIGS. 4 and 5 show a head-mounted display device 1000 including the aroma providing device 1 according to the present embodiment. FIG. 4 is a perspective view of the head-mounted display device 1000 as viewed from the front side, and FIG. 5 is a perspective view of the head-mounted display device 1000 shown in FIG. 4 as viewed from below.

The head-mounted display device 1000 includes a mounting unit 1010, a display unit 1020, and the aroma providing device 1. The display unit 1020 is arranged in front of the eyes of the user and displays an image. The mounting unit 1010 is connected with the display unit 1020 and is mounted on the head of the user so that the display unit 1020 is arranged in front of the eyes of the user.

The aroma providing device 1 is attached to the center of a lower portion of the display unit 1020. The aroma emitted from the aroma emitting device 130 is emitted toward the nasal cavities of the user. Furthermore, the air emitted from the air emitting device 90 is emitted toward the nasal cavities of the user. The aroma providing device 1 receives, for example, an operation signal from a control device (not shown) that controls the display unit 1020 of the head-mounted display device 1000, and emits an aroma or air. Specific usage examples will be described later in detail.

Note that the head-mounted display device 1000 is one of the application examples of the aroma providing device 1, and the aroma providing device 1 may be applied to equipment other than the head-mounted display device 1000.

<2. Configuration Example of Aroma Emitting Device>

Next, an example of the configuration of the aroma emitting device 130 will be described.

(2-1. Overall Configuration Example)

Figure 6:
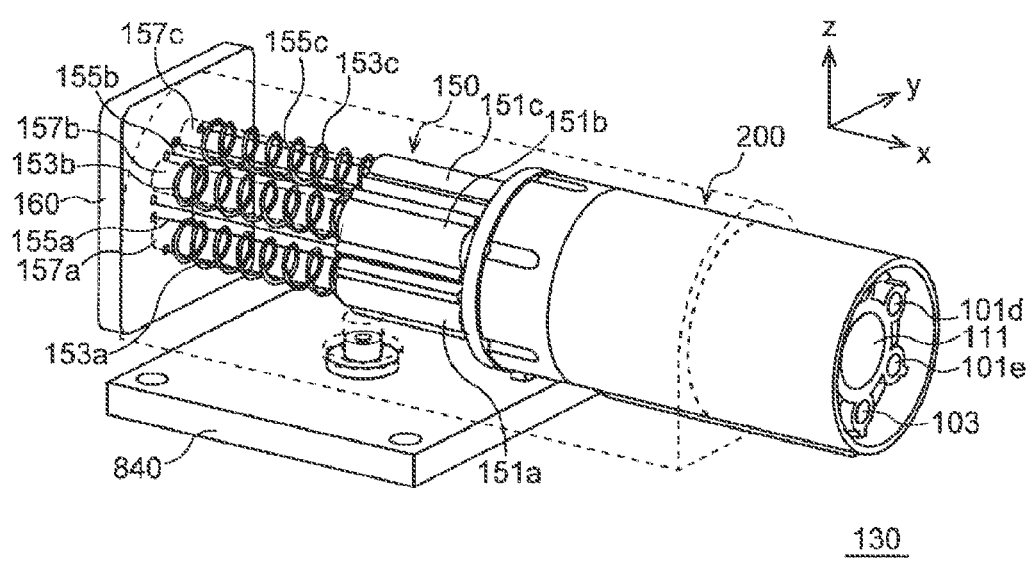
FIG. 6 is a perspective view of an aroma emitting device according to the same embodiment.
Figure 7:
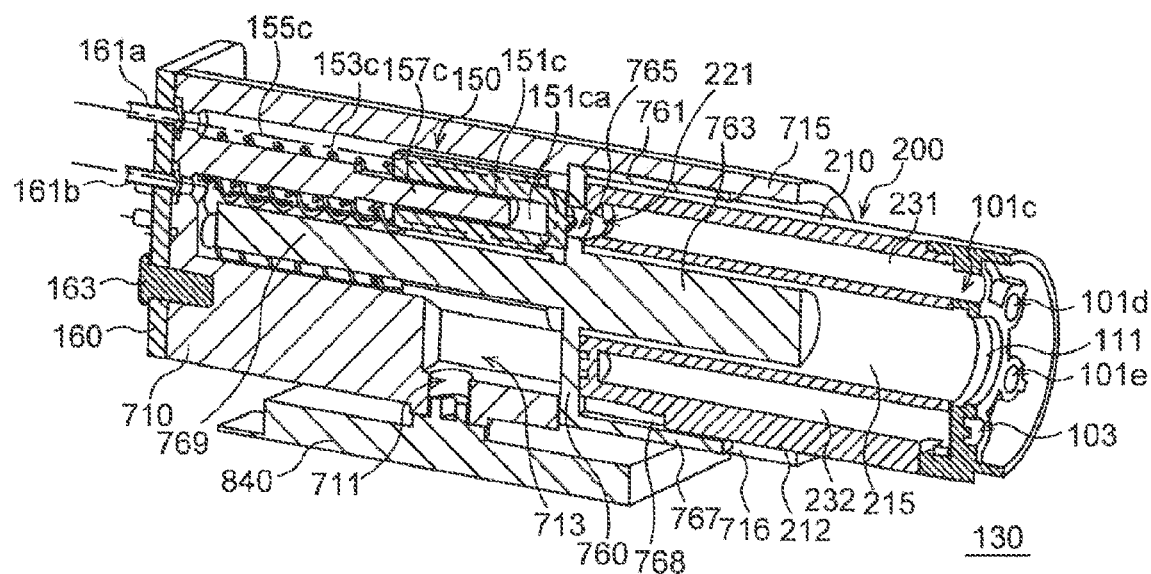
FIG. 7 is a cross-sectional view of an aroma emitting device according to the same embodiment.
Figure 8:
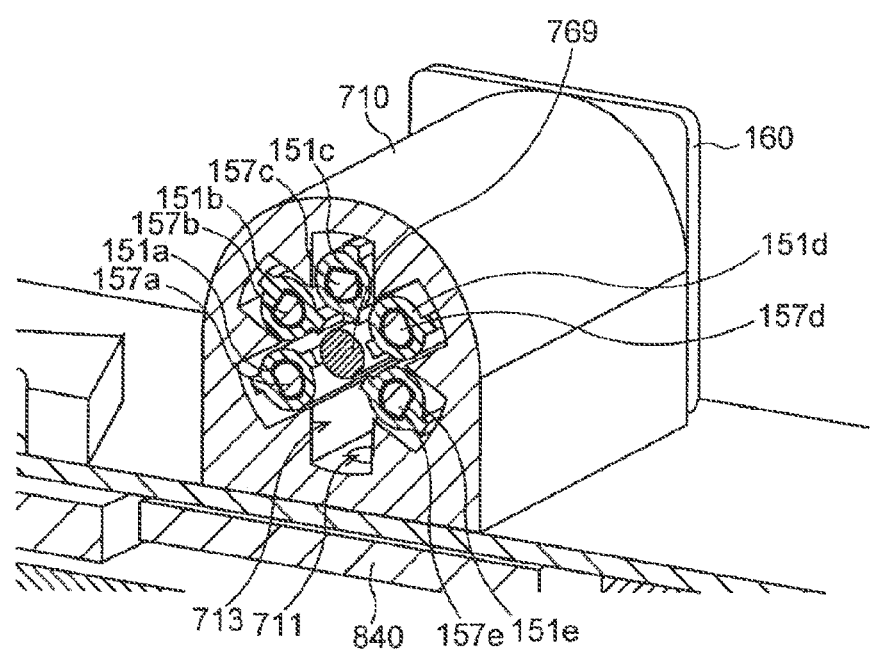
FIG. 8 is a cross-sectional view of an aroma emitting device according to the same embodiment.

FIGS. 6 to 8 are explanatory diagrams showing a configuration example of the aroma emitting device 130. FIG. 6 is a perspective view of the aroma emitting device 130.

FIGS. 7 and 8 are cross-sectional views of the aroma emitting device 130 shown in FIG. 4 cut respectively in the x-direction and the y-direction.

The aroma emitting device 130 includes a housing 710 on which the aromatic cartridge 200 can be mounted. The housing 710 includes a mounting unit 715 on which the aromatic cartridge 200 is to be mounted. A supporting member 760 having a cylindrical portion 761 into which the aromatic cartridge 200 is to be inserted is inserted in the mounting unit 715. At the center of the cylindrical portion 761, a supporting shaft 763 to be fitted with an axial hole 215 provided at the aromatic cartridge 200 is formed coaxially with the cylindrical portion 761.

A protrusion 767 that functions as a positioning element when the supporting member 760 is inserted into the housing 710 is provided on the outer peripheral surface of the cylindrical portion 761 of the supporting member 760. The supporting member 760 is arranged at an appropriate position by inserting the supporting member 760 into the housing 710 with the protrusion 767 aligned with the position of a slit groove 716 provided at the mounting unit 715 of the housing 710.

A protrusion 212 that functions as a positioning element when the aromatic cartridge 200 is mounted on the supporting member 760 is provided on the outer periphery of a case 210 of the aromatic cartridge 200. The aromatic cartridge 200 is arranged at an appropriate position by inserting the aromatic cartridge 200 into the supporting member 760 with the protrusion 212 aligned with the position of a positioning groove 768 provided at the cylindrical portion 761 of the supporting member 760.

The supporting member 760 has air supply ports 765 that penetrate in the axial direction. The air supplied from the first blower device 840 is introduced into holding spaces 231 of the aromatic cartridge 200 through the air supply ports 765. A plurality of the air supply ports 765 is provided so as to correspond to all the holding spaces 231 provided in the aromatic cartridge 200.

The first blower device 840 may be, for example, a diaphragm type pump that deforms a diaphragm by supplying an alternating current to a piezoelectric element to suck and pump air. The battery 810 may be a replaceable battery that only discharges, or may be a rechargeable secondary battery. The drive of the first blower device 840 is controlled by, for example, switching control by the circuit board 820.

Note that the first blower device 840 is not especially limited as long as it can be driven by electric power supplied from the battery 810. In addition to the diaphragm type pump, a blower device of a type that rotates a fan, for example, may be used.

(2-2. Aromatic Cartridge (Aromatic Holding Structure))

Next, an example of the aromatic cartridge 200 that is detachable from the housing 710 will be described in detail. In the present embodiment, an aromatic cartridge having five holding spaces in which the aromatic holders 251 are respectively arranged will be described as an example.

Figure 9:
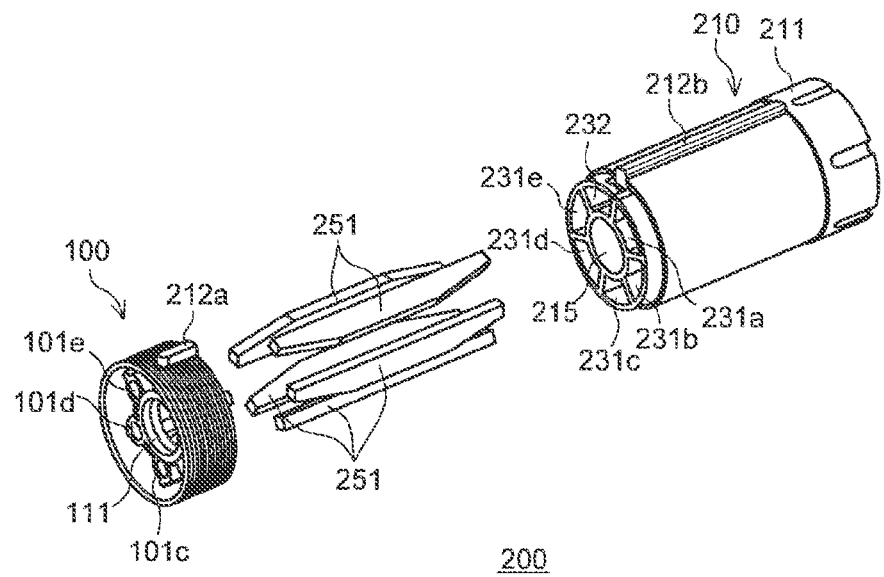
FIG. 9 is an exploded perspective view of an aromatic cartridge.
Figure 10:
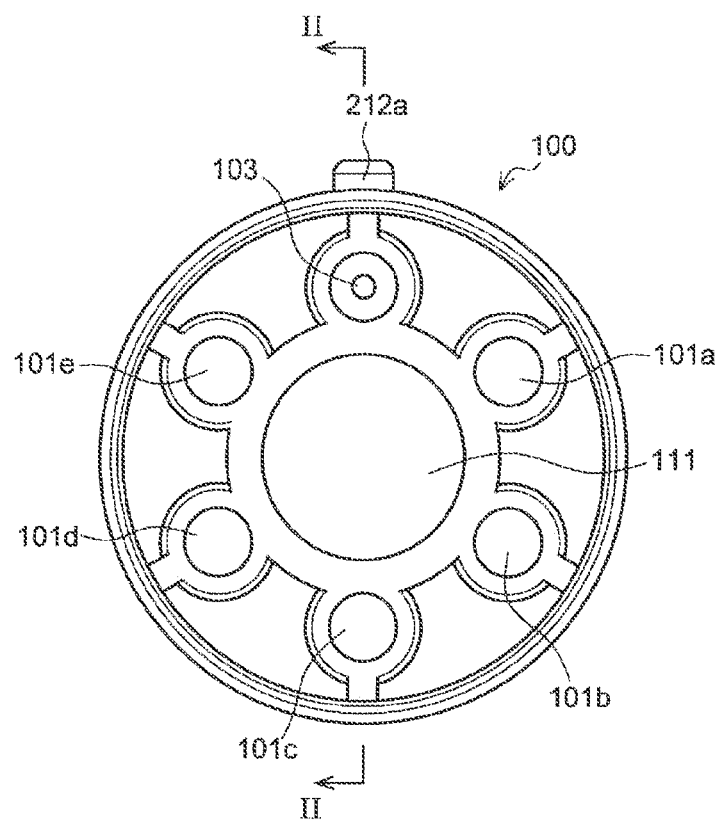
FIG. 10 is a front view of an aromatic cartridge.
Figure 11:
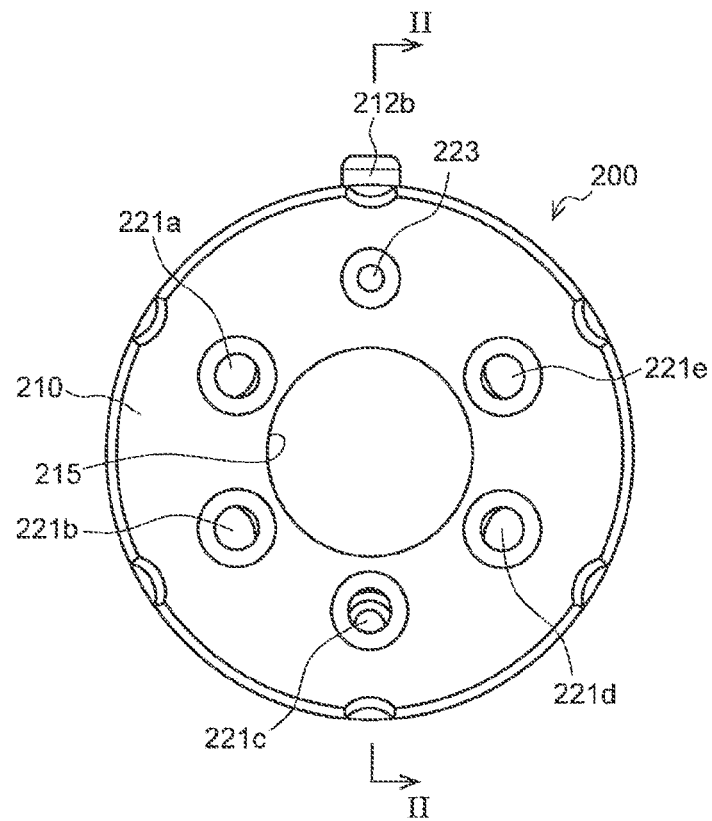
FIG. 11 is a rear view of an aromatic cartridge.
Figure 12:
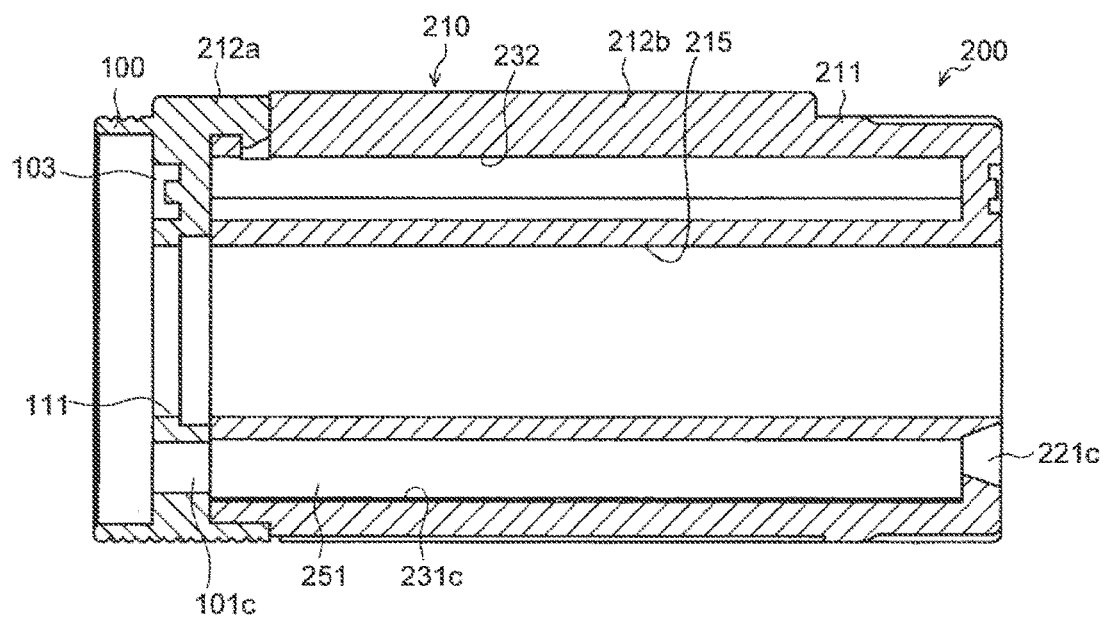
FIG. 12 is an axial sectional view of an aromatic cartridge.

FIGS. 9 to 12 are diagrams for explaining a configuration example of the aromatic cartridge 200. FIG. 9 is an exploded perspective view of the aromatic cartridge 200. FIG. 10 is a front view of the aromatic cartridge 200 viewed from the front side (aroma ejection side) in the axial direction, and FIG. 11 is a rear view of the aromatic cartridge 200 viewed from the rear side (air inflow side) in the axial direction. FIG. 12 is an axial sectional view of the aromatic cartridge 200, and is an arrow view of the I-I cross section shown in FIGS. 10 and 11.

The aromatic cartridge 200 has a cylindrical appearance as a whole. The aromatic cartridge 200 has a plurality of (five in the present embodiment) holding spaces 231a to 231e (collectively referred to as holding spaces 231 hereinafter in a case where distinction is not especially required) that allows the air supplied from the first blower device 840 to pass through. An aromatic holder 251 that holds a liquid aromatic is arranged in each holding space 231. The aromatic may be, for example, an essential oil, an essential oil diluted with ethanol, or the like. The number of the holding spaces 231 may be four or less, or six or more.

The aromatic cartridge 200 according to the present embodiment includes the case 210 and the aromatic holders 251. The case 210 includes a first case body 211, and a second case body 100 fixed to the front side of the first case body 211. An aromatic holder 251 holds a liquid aromatic and is arranged in each of the plurality of holding spaces 231 provided in the case 210. The air introduced into the holding spaces 231 is allowed to pass through even in a state where the aromatic holders 251 are arranged in the holding spaces 231.

For example, each aromatic holder 251 may be a holder obtained by impregnating an impregnation material as a base material with a liquid aromatic. In this case, a porous material or a fiber material including polyester, nylon, felt, polyacetal, or the like can be used as the impregnation material, for example. Furthermore, the impregnation material is preferably a material having resistance to a liquid aromatic. The liquid aromatic may be, for example, an essential oil, an essential oil diluted with ethanol, or the like. The liquid aromatics to be held in the aromatic holders 251 may be different or the same for each holding space 231.

The aromatic cartridge 200 has protrusions 212a and 21b, which function as positioning elements when the aromatic cartridge 200 is mounted, on the outer peripheral surface. The protrusion 212a is provided on the second case body 100, the protrusion 212b is provided on the first case body 211, and the protrusions are formed along the axial direction so as to be connected with each other.

The first case body 211 has a cylindrical outer shape with an axial length larger than the diameter. An axial hole 215 that is open on both end sides in the axial direction is provided in a central portion of the first case body 211. In the first case body 211, five holding spaces 231 are arranged at equal intervals of 60 degrees around the axis, while one space is provided as a pseudo space 232. The plurality of holding spaces 231 and the pseudo space 232 are each open on the front side of the first case body 211. Furthermore, the rear sides of the plurality of holding spaces 231 are open to the outside through the air introduction holes 221 respectively, while the rear side of the pseudo space 232 is closed.

The first case body 211 has the same number of air introduction holes 221a to 221e (collectively referred to as air introduction holes 221 hereinafter in a case where distinction is not especially required) as the number of the holding spaces 231 on the rear end surface. The air introduction holes 221 open the respective holding spaces 231 to the outside. In the present embodiment, five air introduction holes 221a to 221e are arranged at equal intervals of 60 degrees around the axis, together with one pseudo hole 223. The air introduction holes 221 can communicate with the air supply ports 765 of the supporting member 760 inserted in and fixed to the housing 710. The air supply ports 765 and the air introduction holes 221 function as air supply paths through which air is supplied to the respective holding spaces 231. Note that the plurality of holding spaces 231 and the air introduction holes 221 do not have to be arranged at equal intervals.

The second case body 100 has a cylindrical outer shape with an axial length smaller than the diameter. The second case body 100 is engaged with and fixed to the front side end portion of the first case body 211. The outer peripheral surface of the second case body 100 is knurled and is provided with a plurality of fine grooves formed along the circumferential direction.

An axial hole 111 that is open on both end sides in the axial direction is provided in a central portion of the second case body 100. The axial hole 111 of the second case body 100 is integrated with the axial hole 215 of the first case body 211 in a state where the second case body 100 is attached to the first case body 211, so as to form one axial hole. A plurality of (five in the present embodiment) aroma emission holes 101a to 101e (correctively referred to as aroma emission holes 101 hereinafter in a case where distinction is not especially required) that is open on both ends in the axial direction is provided around the axial hole 111. The plurality of aroma emission holes 101 is provided at equal intervals (equal intervals of 60 degrees in the present embodiment) around the axial hole 111, together with one pseudo hole 103. However, the aroma emission holes 101 do not have to be arranged at equal intervals.

In a state where the second case body 100 is attached to the first case body 211, the plurality of aroma emission holes 101a to 101e communicates respectively with the holding spaces 231a to 231e and opens the holding spaces 231a to 231e to the outside. The air introduction holes 221a to 221e provided at the respective holding spaces 231a to 231e, and the respective aroma emission holes 101a to 101e of the second case body 100 are located in the same phase around the axis. That is, the air introduction holes 221 provided at the respective holding spaces 231, and the aroma emission holes 101 are linearly connected with each other along the axial direction.

On the outer peripheral surface of the second case body 100, a protrusion 212a having a predetermined length along the axial direction is provided at a position corresponding to the outer peripheral portion of the position where the pseudo hole 103 is arranged. In a state where the second case body 100 is attached to the first case body 211, the protrusion 212a of the second case body 100 is arranged to be continuous with the protrusion 212b of the first case body 211, so that a protrusion 212 is formed as a unit.

The air introduced into the holding spaces 231 is allowed to pass through the aromatic cartridge 200 according to the present embodiment even in a state where the aromatic holders 251 are arranged therein. When air passes through a holding space 231, the liquid aromatic is vaporized, mixed with air, and emitted. Furthermore, since the space from an air introduction hole 221, which is the supply port of air, to an aroma emission hole 101, which is the emission port, is a closed space without other open ports, all the aromatic vaporized by ventilation can be efficiently emitted from the emission port.

If the aromatic cartridge 200 is detachable from the aroma emitting device 130, only the aromatic cartridge 200 can be easily replaced, and the aroma providing device 1 can be used for a long period of time. Furthermore, since it can be easily replaced with a different aromatic cartridge 200 depending on the purpose, feeling, or the like, different types of aromatics are easily used even in a case where there are not many types of aromatics to be held in one aromatic cartridge 200.

(2-3. Opening/Closing Mechanism)

Returning to FIGS. 6 to 8, the opening/closing mechanism 150 that switches whether to allow air to pass through or not for each holding space 231 will be described in detail.

In the aroma emitting device 130 of the aroma providing device 1 according to the present embodiment, the opening/closing mechanism 150 includes air supply ports 765 and air introduction holes 221, and opens and closes air supply paths through which air is supplied to the holding spaces 231. The opening/closing mechanism 150 includes members that are deformed by a physical stimulus or a chemical stimulus, and switches whether to allow air to pass through or not for each holding space 231.

Figure 14:
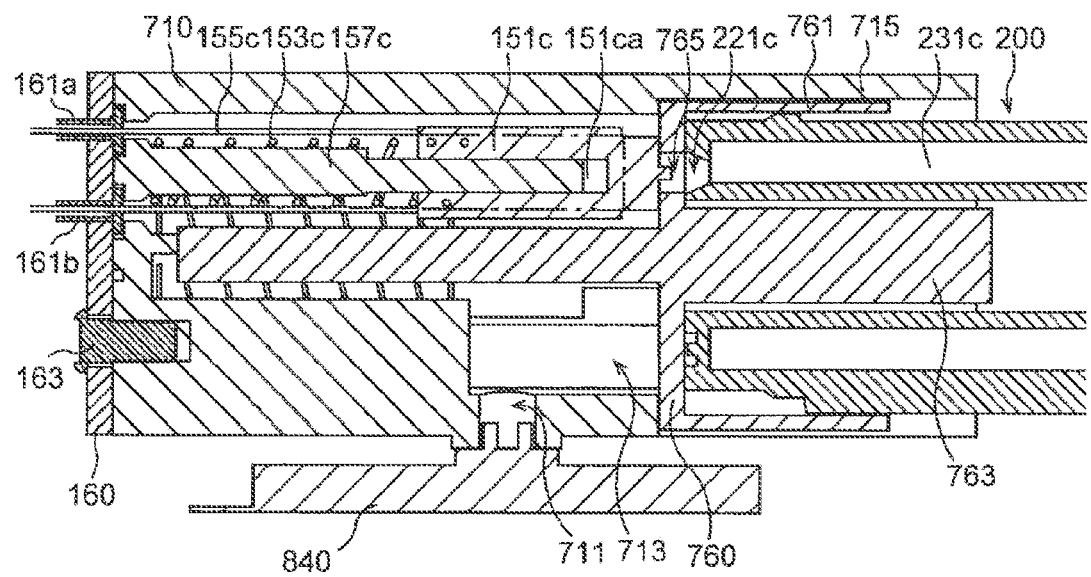
FIG. 14 is a cross-sectional view showing the condition of a non-energized state of a deformable member.

The opening/closing mechanism 150 includes valve members 151, urging members 153, and deformable members 155. A valve member 151, an urging member 153, and a deformable member 155 are independently provided for each air supply port 765 that communicates with each holding space 231 of the aromatic cartridge 200. FIG. 14 shows only the valve member 151c, the urging member 153c, and the deformable member 155c corresponding to the holding space 231c.

A gallery chamber 713 is formed inside the housing 710. A substrate 160 is attached to the rear end surface of the housing 710 so as to cover the gallery chamber 713. The contact part between the housing 710 and the substrate 160 is improved in airtightness by performing treatment such as soldering, for example.

The gallery chamber 713 is connected with the introduction port 711 of air from the first blower device 840 and the air supply ports 765 that communicate with the respective holding spaces 231. At the center of the gallery chamber 713, a rear shaft portion 769 extending rearward from the cylindrical portion 761 of the supporting member 760 is arranged. The valve members 151a to 151e, the urging members 153a to 153e, and the deformable members 155a to 155e are arranged around the rear shaft portion 769, corresponding to the respective holding spaces 231a to 231e. They are collectively referred to as valve members 151, urging members 153, or deformable members 155 hereinafter in a case where distinction is not especially required.

The air introduced into the gallery chamber 713 from the introduction port 711 passes through the gap between the opening/closing mechanism 150 and the rear shaft portion 769 and spreads all over the gallery chamber 713. In the gallery chamber 713, the gap between the opening/closing mechanism 150 and the rear shaft portion 769 is made relatively small, so that the air is quickly supplied to the holding spaces 231 when the first blower device 840 is driven.

The valve members 151a to 151e are respectively supported by the supporting shafts 157a to 157e provided in the gallery chamber 710 to be slidable in the axial direction. Specifically, each valve member 151 is provided with an insertion hole 151ca that is open on the rear side, and the tip portion of the supporting shaft 157 is inserted into the insertion hole 151ca so that the valve member 151 can be supported to be slidable in the axial direction. The tip surface of each valve member 151 can come into contact with the edge surface surrounding an air supply port 765 of the supporting member 760. The supporting shaft 157 and the insertion hole 151ca are processed into a D-shaped cross section, so that the valve member 151 cannot rotate.

Each urging member 153 is arranged between a valve member 151 and the rear end portion of a supporting shaft 157, and urges the valve member 151 in the forward direction, that is, in a direction to close the air supply port 765. In the example of the present embodiment, a coil spring is used as each urging member 153, the tip end portion of the coil spring is embedded in the valve member 151c, and the rear end portion is supported by the rear end portion of the supporting shaft 157c.

Each deformable member 155 is deformed by a physical stimulus or a chemical stimulus to move a valve member 151 in a retreating direction, that is, in a direction to open an air supply port 765, against the urging force of an urging member 153. In the example of the present embodiment, fine wire-shaped shape memory alloy, which is an aspect of a temperature-sensitive deformable member that deforms with a change in temperature, is used as each deformable member 155. The shape memory alloy generates heat due to electrical resistance and deforms during energization.

Figure 13:
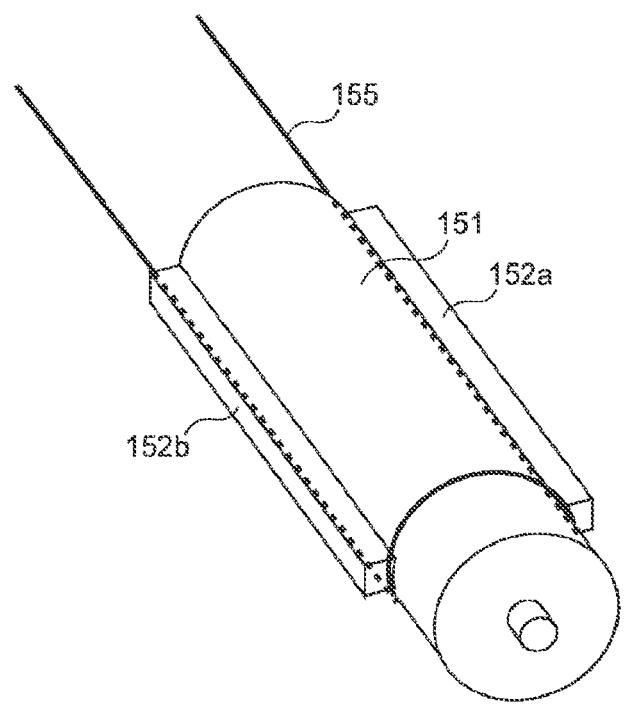
FIG. 13 is a schematic view showing a valve member and a deformable member of an opening/closing mechanism.

FIG. 13 is a schematic view showing a valve member 151 and a deformable member 155. The deformable member 155 including fine wire-shaped shape memory alloy is installed to extend from one overhanging portion 152a of overhanging portions 152a and 152b provided on both side surfaces of the valve member 151 with the central axis interposed therebetween, through the valve member 151 to the other overhanging portion 152b. That is, the deformable member 155 installed with both ends extending rearward is in a state locked to the valve member 151. Although not shown, both ends of the deformable member 155 are electrically connected with the drive circuit of the circuit board 820.

As shown in FIG. 7, both ends of the deformable member 155 are led out of the gallery chamber 713 respectively through the internal holes of eyelets 161a and 161b. Such eyelets 161a and 161b are crimped in a state where the deformable member 155 penetrates the internal holes. Therefore, the deformable member 155 is fixed, and the gallery chamber 713 is improved in airtightness to the outside. The eyelets 161a and 161b may be further subjected to treatment such as soldering to improve the airtightness. At this time, the eyelets 161a and 161b are crimped after the deformable member 155 is subjected to pretension processing. Therefore, the valve member 151 is in a state where the air supply port 765 is closed while the deformable member 155 is in a non-energized state and tension is generated in the deformable member 155, and it is possible to improve the responsiveness until the start of movement of the valve member 151c when the deformable member 155 is energized.

Figure 15:
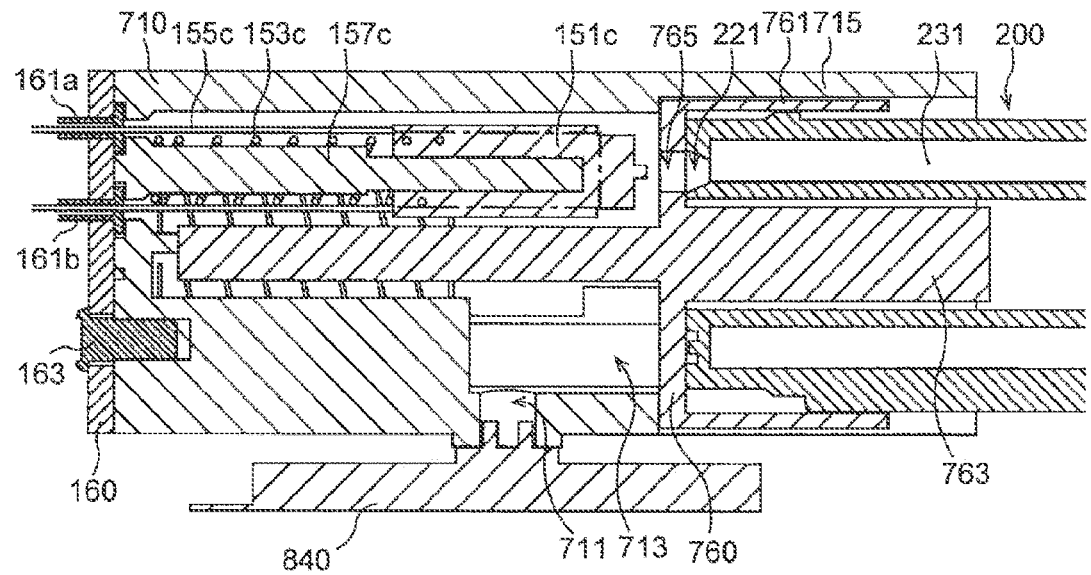
FIG. 15 is a cross-sectional view showing the condition of an energized state of a deformable member.

FIGS. 14 and 15 are explanatory diagrams showing the action of the opening/closing mechanism 150. FIG. 14 is a cross-sectional view showing the condition of the deformable member 155c in a non-energized state, and FIG. 15 is a cross-sectional view showing the condition of the deformable member 155c in an energized state.

In the non-energized state of the deformable member 155c, the valve member 151c is urged in the forward direction by the urging force of an urging member 153, and the air supply port 765 of the supporting member 760 is closed. On the other hand, in the energized state of the deformable member 155c, the valve member 151c retracts against the urging force of the urging member 153 due to contraction of the deformable member 155, and the air supply port 765 of the supporting member 760 is open. Therefore, the air introduced from the first blower device 840 into the gallery chamber 713 is supplied to the holding spaces 231 through the air supply ports 765 and the air introduction holes 221. The air supplied to the holding spaces 231 is emitted from the aroma emission holes 101 together with the aromatic vaporized in the holding spaces 231.

Such valve members 151, urging members 153, and deformable members 155 are provided corresponding to the respective holding spaces 231, and the energization of the respective deformable members 155a to 155e is controlled by the drive circuit of the circuit board 820. Consequently, when an operation signal is inputted into the drive circuit of the circuit board 820 while the blower device 840 is driven, air is supplied to the desired holding space 231 and different aromas can be emitted at arbitrary timings.

At this time, the retraction amount of the valve members 151 may be adjustable according to the quantity of energization supplied to the deformable members 155. Therefore, it is possible to adjust the flow rate of air to pass through the holding spaces 231 even if the amount of air supplied from the first blower device 840 is constant. Furthermore, by supplying air to the plurality of holding spaces 231 while adjusting the retraction amount of the valve members 151, various aromas can be emitted from the aroma emitting device 130 while adjusting the mixing ratio of different aromas.

The configuration of the opening/closing mechanism 150 is not limited to the example described above. Various changes can be made as long as it includes a deformable member that is deformed by a physical stimulus or a chemical stimulus and can open and close the supply path of air supplied to each holding space 231 with the deformation of the deformable member. Here, the deformation due to a physical stimulus or a chemical stimulus means that the shape of the member changes due to energization, an electromagnetic action, a thermal reaction, a humidity change, a photoreaction, a chemical reaction, or the like. A bimetal, an elastic material, and the like may be used as such a deformable member in addition to the shape memory alloy.

Furthermore, the valve members 151 of the opening/closing mechanism 150 are not limited to what moves in the front-rear direction, and may slide in a direction that intersects the axial direction of the air supply path. Furthermore, the opening/closing mechanism may have a throttle function in which the area of the air passage is reduced by the deformation of the deformable member, or may have a door function in which the air passage is opened and closed by the rotation of a rotating plate. Moreover, the opening/closing mechanism may be provided with a member having a hole forming a part of the passage in the middle of the air passage so that the air passage is communicated by moving the member.

<3. Configuration Example of Air Emitting Device>

In a case where different aromas are emitted at short intervals in use of an aroma emitting device capable of emitting a plurality of types of aromas, the aromas are mixed and it becomes difficult for the user to perceive the aroma that the user originally desires to smell. Consequently, the aroma providing device 1 according to the present embodiment includes the air emitting device 90.

As described above, the air emitting device 90 includes the second blower device 91 and the blower duct 93. The blast generated by the second blower device 91 supplied with electric power from the battery 810 is emitted in a predetermined direction through the blower duct 93. The air emission direction of the air emitting device 90 is designed to intersect the aroma emission direction of the aroma emitting device 130.

Consequently, it is possible to scatter away the remaining aroma by air in the vicinity of the position where the air emitted by the air emitting device 90 and the aroma emitted by the aroma emitting device 130 intersect.

Figure 16:
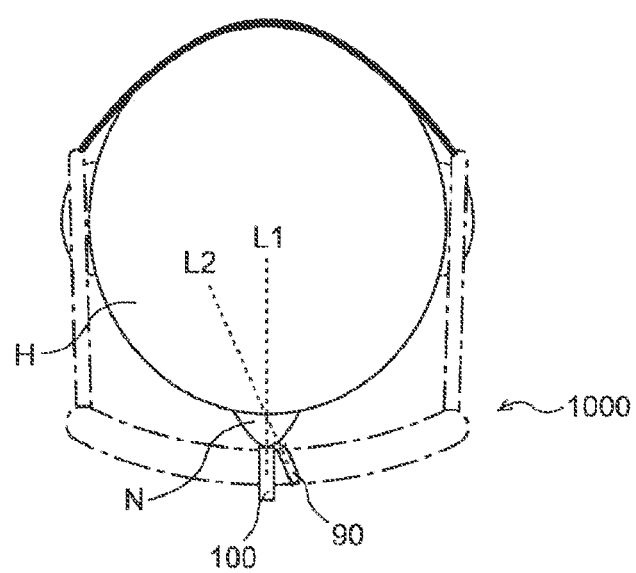
FIG. 16 is an explanatory diagram showing an emission direction of an aroma emitting device and an emission direction of an air emitting device.

FIG. 16 is an explanatory diagram showing an emission direction L1 of the aroma emitting device 130 and an emission direction L2 of the air emitting device 90 of the head-mounted display device 1000 shown in FIGS. 4 and 5. In a case where the user wears the head-mounted display device 1000 shown in FIGS. 4 and 5 on his/her head H, the emission direction L1 of the aroma emitting device 130 and the emission direction L2 of the air emitting device 90 are designed to intersect near the nasal cavities of the nose N of the user. Therefore, in a case where the aroma emitting device 130 sequentially emits different aromas, it is possible to make the user smell the next aroma while scattering away the remaining aroma.

<4. Circuit Configuration Example>

Next, an example of a circuit configuration for driving and controlling the aroma emitting device 130 and the air emitting device 90 of the aroma providing device 1 will be described.

Figure 17:
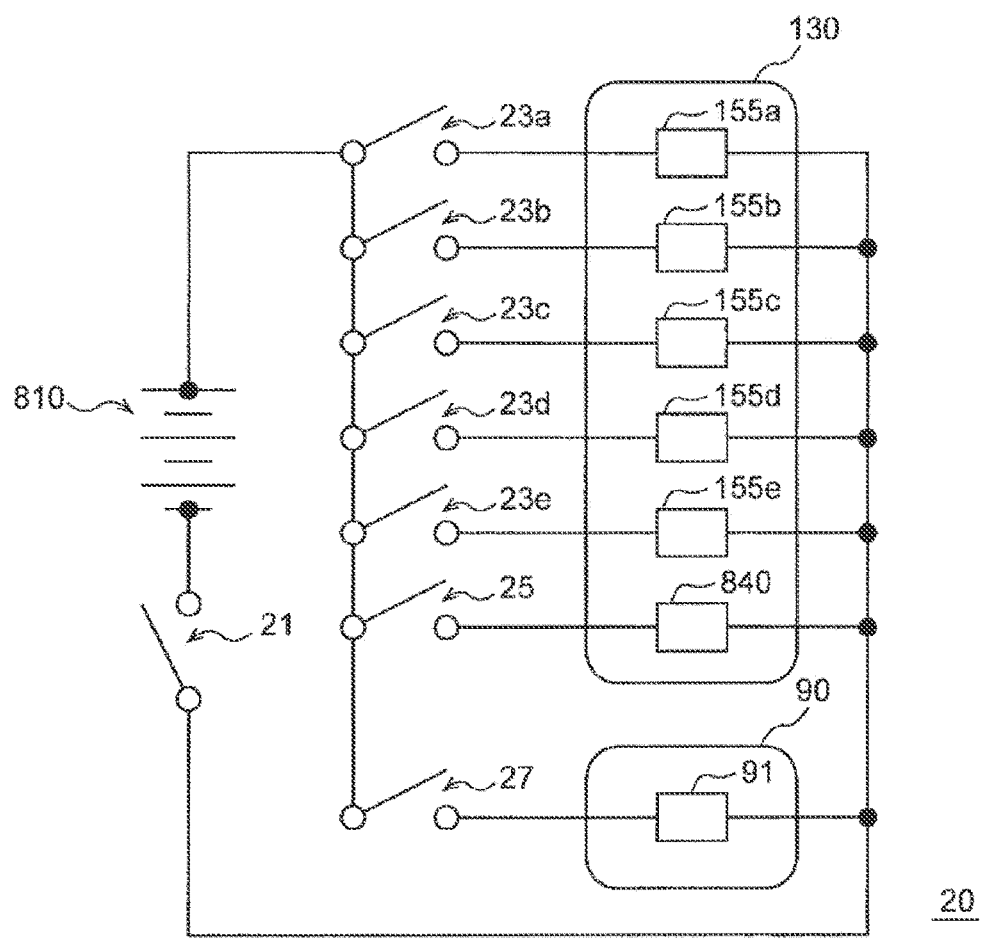
FIG. 17 is an explanatory diagram showing an example of a control circuit of an aroma providing device in a simplified manner.

FIG. 17 is an explanatory diagram showing an example of the control circuit 20 that controls power supply from the battery 810 to the deformable members 155a to 155e, the first blower device 840, and the second blower device 91 in a simplified manner. The control circuit 20 is controlled by a control unit (not shown). The control unit may be, for example, a processor such as a central processing unit (CPU) or a micro processing unit (MPU).

The control circuit 20 includes a main switch 21 that turns on/off power supply of the entire device. Furthermore, the control circuit 20 includes switches 23a to 23e that turn on/off power supply to the respective deformable members 155a to 155e, a switch 25 that turns on/off power supply to the first blower device 840, and a switch 27 that turns on/off power supply to the second blower device 91. The deformable members 155a to 155e, the first blower device 840, and the second blower device 91 are respectively supplied with electric power respectively by turning on the switches 23a to 23e, 25, and 27 with the main switch 21 turned on.

The switches 23a to 23e, 25, and 27 may be linear switches capable of linearly setting the magnitude of the supply current. If the switches 23a to 23e are linear switches, the amount of movement of the valve members 151, that is, the area of the passage of the air supply path can be changed linearly, and the aroma emission flow rate can be adjusted. Furthermore, if the switches 25 and 27 are linear switches, the amount of blast of the first blower device 840 or the second blower device 91 can be changed linearly, and the flow rate of an aroma or air emitted can be adjusted.

The on/off action of the switches 23a to 23e, 25, and 27 of the control circuit 20 may be performed according to a button operation by the user, or may be performed according to an operation signal from the control device.

Furthermore, the control circuit 20 may include a wireless communication interface. Therefore, the aroma providing device 1 can be controlled by receiving an operation signal from an external control apparatus.

<5. Action Example>

Next, an action example of the aroma providing device 1 according to the present embodiment will be described.

The control circuit 20 controls emission of an aroma from the aroma emitting device 130 according to a button operation by the user or an operation signal from the control device. For example, the user may select and emit a desired aroma depending on his/her feeling, or may drive the control circuit 20 so that the control device emits an appropriate aroma according to the content or atmosphere of an image or a moving image viewed by the user.

(5-1. Action Example by User Operation)

Figure 18:
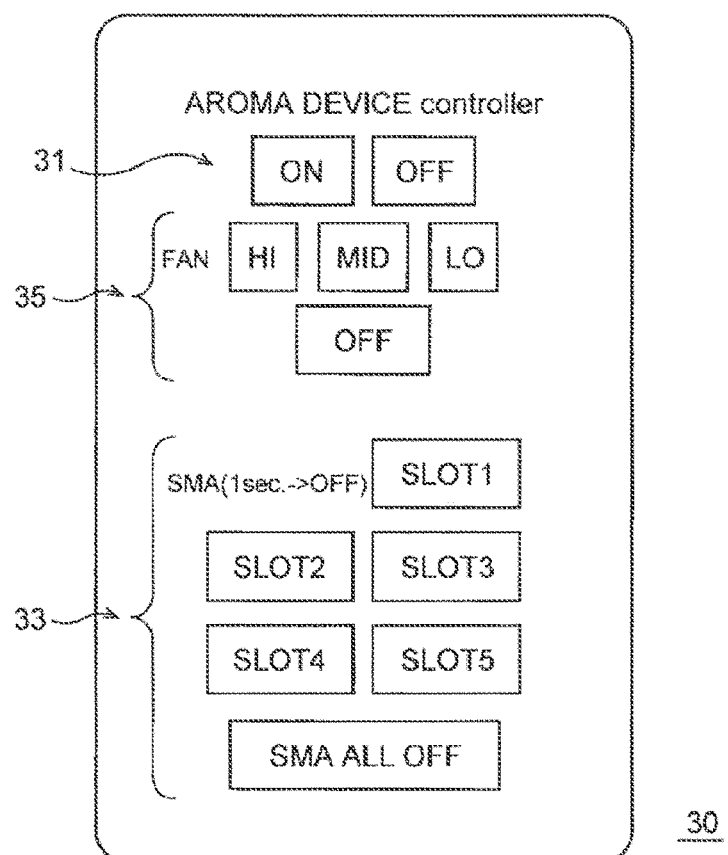
FIG. 18 is an explanatory diagram showing an example of a screen display of an operating apparatus of an aroma providing device.

FIG. 18 shows an example of a screen display 30 of the operating apparatus for the user to control the emission of an aroma and the emission of air. Such an operating apparatus may be a smartphone or a tablet terminal. It may also be a dedicated operating apparatus. The illustrated screen display 30 includes an operation unit 31 for selecting on/off of the main switch 21, an operation unit 33 for selecting the aroma emitted from the aroma emitting device 130, and an operation unit 35 for selecting the flow rate of air emitted from the air emitting device 90. The user can control the emission of an aroma and the emission of air by pressing a desired operation button according to the screen display 30.

The user presses an appropriate operation button depending on a holding space 231 (displayed as SLOT1 to SLOT5 in the figure) according to the type of an aroma to be emitted. In the illustrated example, the control unit opens a valve member 151 leading to a holding space 231 corresponding to the button selected by the user to supply air to the holding space 231 and emit an aroma for a preset time (e.g., one second).

Not only the aroma is selectable, but also the emission time of an aroma may be selectable. For example, the user may be able to select the aroma emission time in three stages (0.3 seconds, one second, and three seconds), so that the valve member 151 is kept open according to the selected time. Moreover, the intensity of the aroma may be selectable. For example, the user may be able to select the intensity of the aroma in three stages (high, medium, and low), so that the opening degree of the valve member 151 is adjusted according to the selected intensity.

Furthermore, in the example shown in FIG. 18, the user can select the air flow rate in three stages (HI/MID/LO). The control unit may cause the air emitting device 90 to constantly emit air according to the selected flow rate. By constantly emitting air, it is possible to scatter away the remaining aroma quickly after making the user smell the aroma emitted, while making the area around the nose of the user odorless during periods other than the period of aroma emission. Accordingly, it is possible to suppress the mixing of an aroma to be emitted next. In this case, the control unit may stop the emission of air only during the period of aroma emission.

Furthermore, the control unit may emit air from the air emitting device 90 after emitting an aroma from the aroma emitting device 130. By emitting air after emitting an aroma, it is possible to scatter away the remaining aroma after making the user smell the aroma emitted. In this case, the control unit may emit air for a preset time or emit a predetermined amount of air, or may adjust the amount of air emitted according to the amount of the aroma emitted. Furthermore, power consumption can be reduced depending on the frequency of aroma emission.

Furthermore, the control unit may emit air from the air emitting device 90 immediately before emitting an aroma from the aroma emitting device 130. That is, the control unit may emit an aroma from the aroma emitting device 130 after emitting air from the air emitting device 90. It is possible to make the user aware of the emission of the aroma by emitting air immediately before the emission of the aroma.

(5-2. Example of Action by Operation Command of Control Device)

The emission of an aroma and the emission of air by the aroma providing device 1 may be controlled on the basis of an operation command from another control device such as a control device that controls the display of a still image or a moving image. For example, the aroma providing device 1 may be controlled in order to form an atmosphere according to the content of a moving image to be reproduced in AR, VR, a movie, or the like. Alternatively, in an attraction facility or the like, the aroma providing device 1 may be controlled in order to form an atmosphere according to the position where the user moves.

Figure 19:
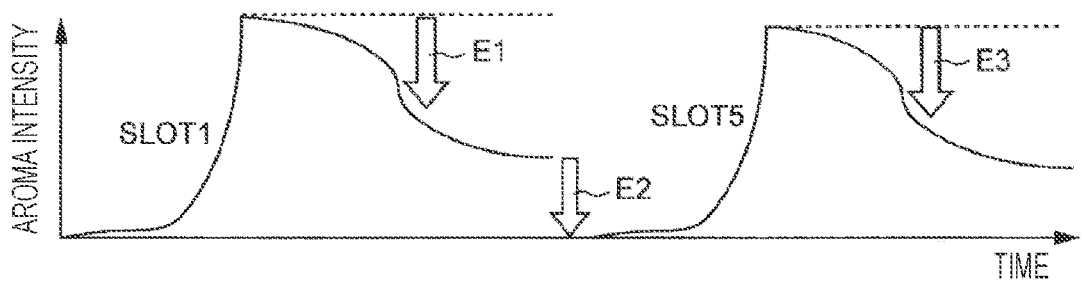
FIG. 19 is an explanatory diagram showing an action example of an aroma providing device.

FIG. 19 shows an action example of the aroma providing device 1 including the aroma emitting device 130 and the air emitting device 90. Such an action example is an action example in which an aroma reminiscent of displayed food is provided to the user while an image of the food is displayed, and is an example in which the aroma emitting device 130 provides an aroma A through one holding space 231 (SLOT1) and then provides an aroma B through another holding space 231 (SLOT5) within a short period of time. In this case, the control device that displays an image is set to output an operation command for generating an appropriate aroma to the control unit of the aroma providing device 1 according to the timing of displaying the image.

In the example shown in FIG. 19, after at least one of the output of the first blower device 840 or the opening degree of the valve member 151 is adjusted so that the intensity of the aroma A emitted from the aroma providing device 1 gradually increases, the second blower device 91 is activated to emit air from the air emitting device 90 (E1 in the figure), and the intensity of the aroma A is reduced. Furthermore, air is emitted from the air emitting device 90 again (E2 in the figure) and the aroma A is scattered away immediately before the aroma B is emitted. After that, at least one of the output of the first blower device 840 or the opening degree of the valve member 151 is adjusted so that the intensity of the aroma B emitted gradually increases. After that, air is emitted after the emission of the aroma B (E3 in the figure), and the intensity of the aroma B is reduced.

In this way, the aroma providing device 1 provides an aroma on the basis of an operation command from another control device in order to form an atmosphere provided to the user. Therefore, in a case where different aromas are provided to the user in a short period of time, the aromas are less likely to be mixed, and the atmosphere provided to the user can be appropriately controlled.

Note that the action of the control unit described above in (5-1.) can be applied to an air emitting method corresponding to the emission of an aroma even in a case where the aroma providing device 1 is caused to act by an operation command of the control device. Furthermore, instead of the configuration example in which information on an action pattern for operating the aroma emitting device 130 and the air emitting device 90 is stored in another control device and an operation command is outputted from the another control device to the aroma providing device 1, information on an action pattern linked to a moving image or the like may be prestored in the control unit of the aroma providing device 130, and the aroma providing device 1 itself may operate the aroma emitting device 130 and the air emitting device 90 according to the action pattern.

<6. Variation>

The aroma emitting device 130 can be modified in various ways other than the examples described above.

For example, although the aroma emitting device 130 and the air emitting device 90 are configured as one unit in the example of the embodiment described above, the aroma emitting device 130 and the air emitting device 90 may be configured separately.

Figure 20:
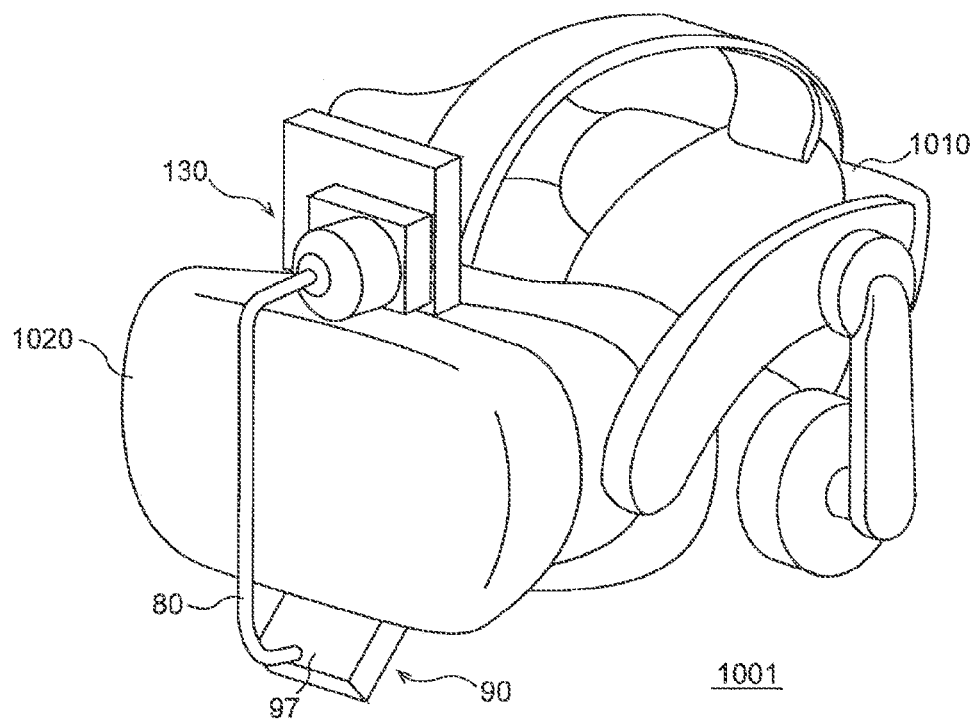
FIG. 20 is a perspective view showing a head-mounted display device including an aroma providing device according to a variation.
Figure 21:
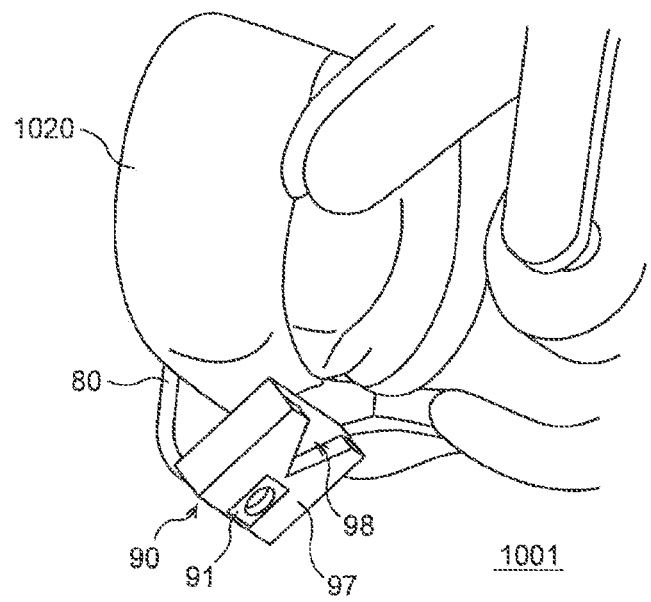
FIG. 21 is a perspective view of a head-mounted display device including an aroma providing device according to a variation as viewed from below.

FIGS. 20 and 21 show a head-mounted display device 1001 provided with an aroma providing device according to a variation. FIG. 20 is a perspective view of the head-mounted display device 1001 as viewed from the front side, and FIG. 21 is a perspective view of a part of the head-mounted display device 1001 shown in FIG. 20 as viewed from the lower side.

The head-mounted display device 1001 according to the variation includes a mounting unit 1010, a display unit 1020, an aroma emitting device 130, and an air emitting device 90, and the aroma emitting device 130 and the air emitting device 90 are arranged separately. The aroma emitting device 130 is arranged above the display unit 1020 to be arranged in front of the eyes of the user, and the air emitting device 90 is arranged below the display unit 1020. The aroma emitting device 130 and the air emitting device 90 are connected with each other by an air supply tube 80, and the aroma emitted from the aroma emitting device 130 is sent to the air emitting device 90 through the air supply tube 80.

The air emitting device 90 includes a blower duct 97 and the second blower device 91. The blower duct 97 has a guide portion 98 on which the nose of the user is to be arranged. The blower duct 97 is open on the end side where the guide portion 98 is provided. The air supply tube 80 is connected with the end portion opposite to the end side on which the guide portion 98 is provided. The aroma sent from the aroma emitting device 130 through the air supply tube 80 passes through the guide portion 98 and is guided to the nose of the user.

The second blower device 91 is capable of discharging air or an aroma in the blower duct 97 to the outside. That is, the air emitting device 90 of the head-mounted display device 1001 shown in FIGS. 20 and 21 is capable of discharging air from the inside of the blower duct 97 instead of emitting the air toward the nasal cavities of the user. Therefore, after the aroma is emitted toward the guide portion 98 on which the nose of the user is arranged, the remaining aroma can be quickly discharged from the inside of the blower duct 97.

Figure 22:
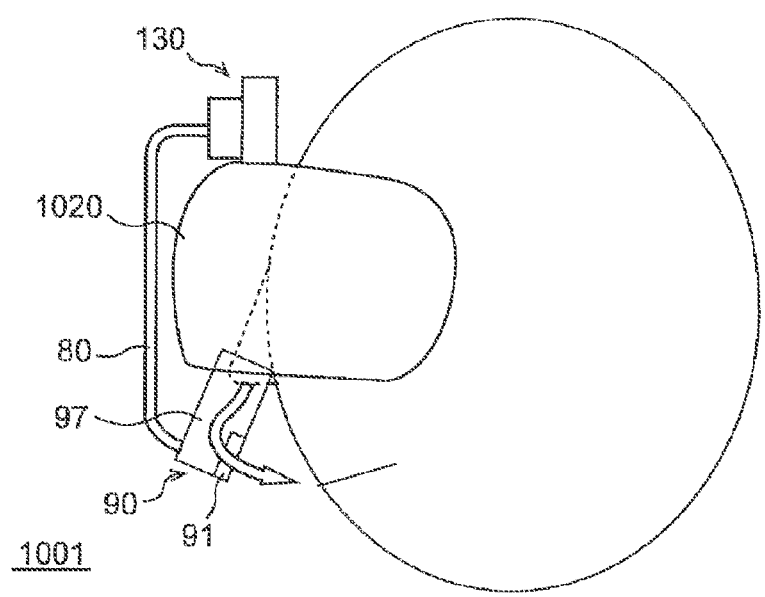
FIG. 22 is an explanatory diagram showing an airflow discharged by an air emitting device of a head-mounted display device including an aroma providing device according to a variation.

The airflow discharged by the second blower device 91 may be directed to the mouth of the user. FIG. 22 is an explanatory diagram showing how the airflow discharged by the second blower device 91 is directed to the mouth of the user. Since the airflow is directed to the mouth of the user, the airflow collides with the vicinity of the mouth and can make the user aware of emission of the aroma in a case where the second blower device 91 acts for a short period of time immediately before emitting the aroma, for example.

Note that the aroma emitting device 130 may be arranged at a position other than above the display unit 1020 in the head-mounted display device 1001 according to the variation shown in FIGS. 20 to 22.

Furthermore, the aroma emitting device 130 may include an aroma mixing chamber into which air that has passed through each holding space 231 of the aromatic cartridge 200 can flow. By providing the aroma mixing chamber, it is possible to allow air to simultaneously pass through a plurality of holding spaces 231 in which different types of aromatics are held and can be emitted after these aromas are mixed in. Accordingly, in the case of an aromatic cartridge capable of holding five types of aromas, for example, a total of 30 types of aromas can be emitted by one type alone or a combination of a plurality of types.

Furthermore, in a case where the aroma mixing chamber is provided, a configuration for generating a stirring flow may be provided inside the aroma mixing chamber. For example, a fin standing up from the inner wall surface of the aroma mixing chamber may be provided, or a static mixer capable of generating a stirring flow may be provided inside the aroma mixing chamber.

Furthermore, although the opening/closing mechanism 150 of the aroma emitting device 130 described above opens and closes the air supply paths to the holding spaces 231, the opening/closing mechanism may open and close aroma emission paths from the holding spaces 231. Since air cannot pass through a holding space 231 even in a case where the aroma emission path is closed, the opening/closing mechanism can switch whether an aroma can be emitted or not. In a case where the opening/closing mechanism is configured to open and close the aroma emission path, it is possible to prevent leakage of an aroma from a holding space 231 other than the holding space 231 that allows air to pass through. On the other hand, in a case where the opening/closing mechanism is configured to open and close the air supply path, it is possible to prevent members constituting the opening/closing mechanism from being damaged by erosion by a liquid aromatic and the like.

Furthermore, the opening/closing mechanism 150 may be provided on both the air supply path and the aroma emission path. Therefore, it is possible to enhance the effect of preventing leakage of the aroma from a holding space 231 that does not allow air to pass through.

Furthermore, the aroma providing device 1 may include a plurality of aromatic cartridges and a plurality of opening/closing mechanisms. In this case, a plurality of aromatic cartridges may be arranged in series so that the air supplied from the first blower device 840 sequentially passes through the plurality of aromatic cartridges. By allowing air to pass through a plurality of aromatic cartridges, different aromas can be mixed, or the intensity of the same aroma can be increased.

Furthermore, the aroma providing device 1 may include a plurality of aroma emitting devices 130. Therefore, more types of aromas can be emitted. In this case, each of the plurality of aroma emitting devices 130 may include the first blower device 840, or some or all of the plurality of aroma emitting devices 130 may include a common first blower device 840. Therefore, it is possible to emit various aromas. Furthermore, a plurality of aroma emitting devices 130 may be provided so that emission ports of aromas from the plurality of aroma emitting devices 130 face each other. Therefore, the aromas can be easily mixed and emitted.

Furthermore, at least one of the plurality of holding spaces 231 of the aromatic cartridge 200 may be used without holding an aromatic. For example, it is possible to reduce the intensity of the aroma by allowing air to pass through a holding space 231 in which no aromatic is held, while allowing air to pass through one of the holding spaces 231 in which an aromatic is held. Furthermore, by providing a holding space 231 in which no aromatic is held, odorless air can be emitted, and the air emitting device 90 can be omitted. Moreover, a deodorant such as activated carbon may be held instead of holding an aromatic. Therefore, the deodorizing effect of the remaining aroma can be enhanced.

Furthermore, in the aroma providing device 1 according to the embodiment described above, at least one of the aroma emission direction or the air emission direction may be adjustable. Therefore, the emission direction of an aroma or air can be adjusted according to the preference of the user.

As described above, it is possible with the aroma providing device 1 according to the present embodiment to replace or replenish an aromatic easily only by replacing the aromatic cartridge 200, since the aroma providing device includes the aroma emitting device 130 that uses the detachable aromatic cartridge 200 having a plurality of holding spaces 231 in which aromatics are respectively held. Accordingly, the aroma providing device 1 can be used for a long period of time.

Furthermore, since the aroma providing device 1 according to the present embodiment includes the opening/closing mechanism 150 that switches whether to allow air to pass through or not for each of the plurality of holding spaces 231, an aromatic emitted can be switched quickly. Furthermore, since the aroma providing device 1 includes the opening/closing mechanism 150 that switches whether to allow air to pass through or not for each of the plurality of holding spaces 231, it is possible to allow air to pass through the plurality of holding spaces 231 simultaneously, and to emit aromas while mixing the same. Furthermore, since the opening/closing mechanism 150 is a mechanism including the deformable members 155 that are deformed by a physical stimulus or a chemical stimulus, vibration and vibration during operation can be reduced.

Furthermore, the aroma providing device 1 according to the present embodiment includes the air emitting device 90 and can replace air around the nose by emitting air toward the nose of the user or blowing air away from the vicinity of the nose of the user. Consequently, it is possible to eliminate the aroma or make preparations for switching the aroma. Furthermore, the intensity of the aroma may be adjusted by adjusting the amount of air emitted from the air emitting device 90, instead of adjusting the amount of an aroma emitted from the aroma emitting device 130 or together with adjusting the amount of the aroma emitted.

Although a preferred embodiment of the present disclosure has been described in detail with reference to the accompanying drawings, the technical scope of the present disclosure is not limited to such examples. It is clear that anyone with ordinary knowledge in the technical field of the present disclosure may come up with various change examples or modification examples within the scope of the technical ideas set forth in the claims, and it is to be understood of course that these belong to the technical scope of the present disclosure.

Note that the following configurations also belong to the technical scope of the present disclosure.

(1) An aroma providing device including:
an aromatic holding structure that is detachable and has a plurality of holding spaces in which aromatics are respectively held;
a blower device that supplies air to pass through the holding spaces;
a plurality of air supply paths through which the air is introduced into the respective holding spaces;
an opening/closing mechanism that includes a member that is deformed by a physical stimulus or a chemical stimulus and switches whether to allow the air to pass through or not for each of the holding spaces; and
a control unit that controls the opening/closing mechanism.

(2) The aroma providing device according to (1), in which the opening/closing mechanism includes:
a valve member that closes a flow path of the air;
an urging member that urges the valve member in a direction to close a flow path of the air; and
a deformable member that is deformed by a physical stimulus or a chemical stimulus to move the valve member in a direction to open a flow path of the air.

(3) The aroma providing device according to (1) or (2), in which the deformable member is a temperature-sensitive deformable member that is deformed with a change in temperature.

(4) The aroma providing device according to (3),
in which the temperature-sensitive deformable member is a shape memory alloy, a bimetal, or an elastic material.

(5) The aroma providing device according to (2), in which the deformable member is a fine wire-shaped shape memory alloy, and
the fine wire-shaped shape memory alloy is deformed by a change in temperature due to energization to move the valve member against an urging direction of the urging member and open a flow path of the air.

(6) The aroma providing device according to (5),
in which the valve member closes a flow path of the air in a state where tension is generated in the fine wire-shaped shape memory alloy in a non-energized state of the fine wire-shaped shape memory alloy.

(7) The aroma providing device according to any one of (1) to (6),
in which the opening/closing mechanism is provided on any of the air supply paths.

(8) The aroma providing device according to any one of (1) to (7), further including
a gallery chamber, into which air supplied from the blower device is introduced, connected with the plurality of air supply paths.

(9) The aroma providing device according to (8),
in which the opening/closing mechanism is provided on any of the air supply paths,
the deformable member is fine wire-shaped shape memory alloy,
at least a part of the fine wire-shaped shape memory alloy is arranged in the gallery chamber,
the fine wire-shaped shape memory alloy is led out of the gallery chamber through an internal hole of an eyelet, and
the fine wire-shaped shape memory alloy is fixed by crimping the eyelet, and the gallery chamber is closed to the outside.

(10) The aroma providing device according to any one of (1) to (9), further including
an aroma mixing chamber into which air that has passed through the respective holding spaces can flow.

(11) An aroma providing device including:
an aroma emitting unit that can selectively emit an aroma selected from a plurality of aromas;
an air emitting unit that can emit air toward a reachable range of the aroma emitted; and
a control unit that controls the aroma emitting unit and the air emitting unit.

(12) The aroma providing device according to (11),
in which an aroma emission direction of the aroma emitting unit and an air emission direction of the air emitting unit intersect.

(13) The aroma providing device according to (12),
in which the aroma providing device is used in a state mounted on the head of a user, and the aroma emission direction of the aroma emitting unit and the air emission direction of the air emitting unit intersect around the nostrils of the user.

(14) The aroma providing device according to (11),
in which the control unit
constantly emits the air from the air emitting unit with a main power of the aroma providing device turned on.

(15) The aroma providing device according to (14),
in which the control unit
stops emission of the air during a period of aroma emission from the aroma emitting unit.

(16) The aroma providing device according to (11),
in which the control unit
causes the air emitting unit to emit the air after causing the aroma emitting unit to emit an aroma.

(17) The aroma providing device according to (11),
in which the control unit
causes the aroma emitting unit to emit an aroma after causing the air emitting unit to emit the air.

(18) The aroma providing device according to (11),
in which the control unit
adjusts intensity of the aroma emitted, by adjusting the amount of air emitted from the air emitting unit.

(19) The aroma providing device according to (11),
in which the aroma providing device is used in a state mounted on the head of a user and includes a blower duct having a guide portion on which the nose of the user is to be arranged,
an aroma emitted from the aroma emitting device is emitted toward the guide portion through the blower duct, and
the air emitting device discharges air or an aroma in the blower duct to outside of the blower duct.

(20) The aroma providing device according to (19),
in which an airflow discharged to outside of the blower duct by the air emitting device is directed to the mouth of the user.

(21) A head-mounted display device including:
a mounting unit to be mounted on the head of a user;
a display unit arranged in a line-of-sight direction of the user when worn by the user; and
an aroma providing device,
the aroma providing device including:
an aroma emitting unit that can selectively emit an aroma selected from a plurality of aromas;
an air emitting unit that can emit air toward a reachable range of the aroma emitted; and
a control unit that controls the aroma emitting unit and the air emitting unit.

REFERENCE SIGNS LIST

1 Aroma providing device
20 Control circuit
90 Air emitting device
91 Second blower device
93 Blower duct
151 Valve member
153 Urging member
155 Deformable member
200 Aromatic holding structure (aromatic cartridge)
221c Air introduction hole
231 Holding space
765 Air supply port
810 Battery
820 Circuit board
840 First blower device

The invention claimed is:
1. An aroma providing device, comprising:
an aromatic holding structure that is detachable from the aroma providing device, wherein
the aromatic holding structure has a plurality of holding spaces in which plurality of aromatics are respectively held;
a blower device configured to supply air to pass through the plurality of holding spaces;

a plurality of air supply paths through which the air is introduced into the plurality of holding spaces;

an opening and closing mechanism that includes a deformable member, wherein the deformable member is deformed by one of a physical stimulus or a chemical stimulus, and the opening and closing mechanism is configured to switch between an open state and a close state to allow the air to pass through each of the plurality of holding spaces; and a control unit configured to control the opening and closing mechanism.

2. The aroma providing device according to claim 1, wherein the opening and closing mechanism comprises:

a valve member that closes a flow path of the air;

an urging member that urges the valve member in a first direction to close the flow path of the air; and the deformable member that moves the valve member in a second direction to open the flow path of the air, wherein the second direction is different from the first direction.

3. The aroma providing device according to claim 1, wherein the deformable member is a temperature-sensitive deformable member that is deformed with a change in temperature.

4. The aroma providing device according to claim 3, wherein the temperature-sensitive deformable member is one of a shape memory alloy, a bimetal, or an elastic material.

5. The aroma providing device according to claim 2, wherein the deformable member is a fine wire-shaped shape memory alloy, and the fine wire-shaped shape memory alloy is deformed by a change in temperature due to energization to move the valve member against the first direction of the urging member and open the flow path of the air.

6. The aroma providing device according to claim 5, wherein the valve member closes the flow path of the air based on generation of tension in the fine wire-shaped shape memory alloy in a non-energized state of the fine wire-shaped shape memory alloy.

7. The aroma providing device according to claim 1, wherein the opening and closing mechanism is on at least one of the plurality of the air supply paths.

8. The aroma providing device according to claim 1, further comprising a gallery chamber, into which air is supplied from the blower device, connected with the plurality of the air supply paths.

9. The aroma providing device according to claim 8, wherein the opening and closing mechanism is on at least one of the plurality of the air supply paths, the deformable member is fine wire-shaped shape memory alloy, at least a part of the fine wire-shaped shape memory alloy is in the gallery chamber, the fine wire-shaped shape memory alloy is led out of the gallery chamber through an internal hole of an eyelet, the fine wire-shaped shape memory alloy is fixed by crimping the eyelet, and the gallery chamber is closed to an outside.

10. The aroma providing device according to claim 1, further comprising an aroma mixing chamber into which air that has passed through the plurality of holding spaces flows.

* * * * *